(12) United States Patent
Pert et al.

(10) Patent No.: US 6,713,445 B1
(45) Date of Patent: Mar. 30, 2004

(54) PEPTIDES FOR TREATMENT OF HIV INFECTION

(75) Inventors: Candace Pert, Potomac, MD (US); Michael Ruff, Potomac, MD (US)

(73) Assignee: Advanced Immuni T, Inc., Stony Brook, NY (US)

( * ) Notice: Subject to any disclaimer, the term of this patent is extended or adjusted under 35 U.S.C. 154(b) by 0 days.

(21) Appl. No.: 09/647,749

(22) PCT Filed: Apr. 6, 1999

(86) PCT No.: PCT/US99/07514

§ 371 (c)(1),
(2), (4) Date: Jun. 12, 2001

(87) PCT Pub. No.: WO99/51254

PCT Pub. Date: Oct. 14, 1999

Related U.S. Application Data
(60) Provisional application No. 60/080,836, filed on Apr. 6, 1998.

(51) Int. Cl.[7] .......................... A61K 38/00; C07K 7/00
(52) U.S. Cl. .......................... 514/2; 530/300; 530/329; 530/330; 514/4; 514/12
(58) Field of Search .................. 514/2, 4, 12; 530/300, 530/329, 330

(56) References Cited

U.S. PATENT DOCUMENTS

| | | | | |
|---|---|---|---|---|
| 5,567,682 A | * | 10/1996 | Pert ............................ | 514/15 |
| 5,641,746 A | * | 6/1997 | Steinman ...................... | 514/12 |
| 5,972,883 A | * | 10/1999 | Gozes et al. .................... | 514/12 |
| 6,217,886 B1 | * | 4/2001 | Onyuksel et al. ............ | 424/401 |
| 6,239,107 B1 | * | 5/2001 | Gozes et al. ................... | 514/14 |
| 2003/0113270 A1 | * | 6/2003 | Clark .......................... | 424/45 |

FOREIGN PATENT DOCUMENTS

EP  0 620 008 A1 * 10/1994 .......... A61K/37/02

OTHER PUBLICATIONS

Brenneman et al. (Oct. 13, 1998) "Neuronal cell killing by the envelope protein of HIG and its prevention by vasoactive intestinal peptide." Nature 33(6191): 639–642.*
Buzy et al. (1992) "Potent gp120–like neurotoxic activity in the cerebrospinal fluid of HIV–infected individuals is blocked by peptide T." Brain Research 598(1–2): 10–18.*
Offen et al. (2000) "Apoptosis as a general cell death pathway in neurodegenerative diseases." J. Neural. Transm. [Suppl] 58: 153–166.*
Sacerdote et al. (1987) "Vasoactive Intestinal Peptide 1–12: A Ligand for the CD4 (T4)/Human Immunodeficiency Virus Receptor." Journal of Neuroscience Research 18(1): 102–107.*
Gozes et al. (Jan. 1996) Neuroprotective strategy for Alzheimer disease: Intranasal administration of a fatty neuropeptide. PNAS 93: 427–432.*
Fournier et al. (May–Jun. 1982) "400 MHz NMR study on the C–terminal fragment of 21–28 of vasoactive intestinal peptide," Peptides 3(3): 345–352.*
Said et al. (Feb. 1998) "Enhancement of Systemic and Pulmonary Vasoconstriction by b–Amyloid Peptides and its Suppression by Vasoactive Intestinal Peptide." Annals of the New York Academy of Sciences 865: 582–585.*
Onoue et al. (Aug. 2002) "The neuropeptide PACAP attenuates beta–amyloid (1–42)–induced toxicity in PC12 cells." Peptides 23(8): 1471–1478.*
Gozes et al. (Apr. 24, 1997) "Neuropeptides and neuronal survival: neuroprotective strategy for Alzheimer's disease." Annals o the New York Academy of Science 814: 161–166.*
Yanaihara et al. (Mar.–Apr. 1984) "Immunochemical study of PHI/PHM with use of synthetic peptides." Peptides 5(2): 247–25.*
Veijkovic et al. (Dec. 15, 1992) "Spectral and sequence similarity between vasoactive intestinal peptide . . . " Biochemical an Biophysical Research Communications 189(2): 705–710.*
Haghjoo et al. (Nov.–Dec. 1996) "Solution Structure of Vasoactive Intestinal Polypeptide (11–28)–NH2, a Fragment with Analgesic Properties," Peptide Research 9(6): 327–331.*
Romualdi et al. (May–Jun. 1989) "Vasoactive Intestinal Polypeptide Carboxy–Terminal Fragment, VIP(22–28), and Other Fragments of VIP, in the Central Nervous System of the Rat." Peptides 10(3): 621–626.*
Goossens et al. (Jan. 1992) "Antagonistic effect of a vasoactive intestinal peptide fragment, vasoactive intestinal peptide(1–11), on guinea pig smooth muscle relaxation."0 Molecular Pharmacology 41(1): 104–109.*
Gozes et al. (Sep. 1997) "Protection against developmental retardation in apolipoprotein E–deficient mice by a fatty neuropeptide: implications for early treatment of Alzheimer's disease." J Neurobiol. 33(3): 329–342.*

* cited by examiner

Primary Examiner—Elizabeth Kemmerer
Assistant Examiner—Christopher James Nichols
(74) Attorney, Agent, or Firm—William J. Sapone; Coleman Sudol Sapone, P.C.

(57) ABSTRACT

The HIV-1 envelope protein gp120 is toxic to rodent and human neurons by indirect mechanisms requiring accessory glial cells. Chemokines are known to block gp120 interactions with chemokine receptors on T cells, macrophanges, and microglia, thereby preventing viral infection. Gp120-induced neuronal killing in rat hippocampal cultures was partially or completely prevented by a specific short peptides related to chemokines, specially IKEYFTS (SEQ. ID NO: 2) and LESYT (SEQ. ID NO: 1). These peptides thus have use in the treatment of neurological degenerative diseases having symptoms associated with neuronal cell death.

10 Claims, 1 Drawing Sheet

```
                           SEQUENCE LISTING

<160> NUMBER OF SEQ ID NOS: 3

<210> SEQ ID NO 1
    <211> LENGTH: 5
    <212> TYPE: PRT
    <213> ORGANISM: mammalian

<400> SEQUENCE: 1

Leu Glu Ser Tyr Thr
    1               5

<210> SEQ ID NO 2
    <211> LENGTH: 7
    <212> TYPE: PRT
    <213> ORGANISM: mammalian

<400> SEQUENCE: 2

Ile Lys Glu Tyr Phe Thr Ser
    1               5

<210> SEQ ID NO 3
    <211> LENGTH: 5
    <212> TYPE: PRT
    <213> ORGANISM: mammalian

<400> SEQUENCE: 3

Ile Lys Glu Tyr Phe
    1               5
```

PEPTIDES FOR TREATMENT OF HIV INFECTION

This application is a 371 of PCT/US99/07514 filed Apr. 6, 1999 which claims benefit of Ser. No. 60/080,836 filed Apr. 6, 1998.

TECHNICAL FIELD

This invention is directed to synthetically produced short peptide sequences which inhibit HIV-1 gp120 induced neuronal cell death, for use in preventing neurological deterioration in patients suffering from AIDS as well as other neurological degenerative diseases.

BACKGROUND

Among the symptoms and conditions associated with HIV infection (AIDS) are specific neurological conditions which can be termed "neuro-AIDS".

Neuro-AIDS, whose incidence and severity appears to be increasing, can manifest itself in many forms including encephalopathies, neuropathies, memory loss, dementia, depression, psychosis and opportunistic infections. One explanation for AIDS associated neuropathologies, which can include infiltration of infected immune cells, white matter aberrations, reduced dendritic and axonal arborization, and neuronal loss is that dissociated HIV envelop protein, gp120, which has been shown to be secreted abundantly by infected macrophages and is present in plasma and CSF, contributes to pathogenesis via receptor-mediated interactions with various shared cell surface receptors on brain and immune cells.

There is growing evidence that neurotoxicity and infectivity associated with HIV have distinctive attributes suggesting divergence of mechanism. In particular, HIV infection does not occur in rodents and does not require signaling, while the biological activities associated with the envelope protein can be demonstrated in both human and rodent cells and requires signaling. The neurotoxic action of HIV-1 envelope protein gp120 is potent and requires the presence of glial cells, which may then secrete neurotoxic products or cytokines. In rodents, intraventriculary administered gp120 produces endocrine abnormalities.

The neuropeptide vasoactive intestinal peptide (VIP), as well as homologous short (5–8 residues) peptides derived from the gp120 V2 region derived peptides (8–10) are inhibitors of gp120 neurotoxicity. In neonatal rats, delayed behavioral milestones and abnormal neuronal dearborization produced by administration of nanogram quantities of gp120 are also prevented by VIP (II) and gp120 V2-region derived peptide T ("DAPTA"). In the same study, toxic fragments of gp120 were recovered from treated animals, suggesting that some of the neural damage is attributable to proteolytic products of the HIV envelope.

Alzheimers' Disease or dementia is believed to be caused by the deterioration of the cholinergic neurons in the basal forebrain. VIP is co-localized with cholinergic neurons in the basal forebrain and is believed to maintain neuronal survival. In a proposed secondary phase of Alzheimers' disease, endogenous neurons of the cortex of various different chemical types degenerate following deprivation of their vasoactive intestinal polypeptide neuronal growth factor once contained in the cholinergic endings.

In U.S. Pat. No. 5,567,682, short chain peptides, specifically peptide T and related analogs, are described for treating the symptoms of Alzheimers' disease by reducing or halting a loss of neurons. Similarly, these peptides are described as being useful in inhibiting HIV-1 binding to T4 cell receptors (U.S. Pat. No. 5,276,016).

Recent discoveries show that HIV gp120 uses a number of chemokine co-receptors, in conjunction with CD4, to allow viral entry of target cells. Moreover, various gp120's can block binding of specific chemokine ligands with the CCR5 receptor. Chemokine receptors, first characterized on activated immune cells, have been shown to also be present on cerebellar neuronal processes, differentiated human neuronal lines, and both microglial cells and astrocytes in human brain cultures. Thus the inventors sought to identify novel short chemokine peptides which would be antagonists of gp120-mediated neurotoxicity and resultant neuronal degeneration and thereby provide therapeutic benefits in patients suffering from HIV infection, or other inflammatory neurological diseases such as multiple sclerosis, tropical spastic paraparesis, and Alzheimers, to cite some.

SUMMARY OF THE INVENTION

It is an object of the present invention to provide peptides and a method for treating diseases having symptoms caused by neuronal cell death caused by HIV, MS, Alzheimers' Disease, PML, and Tropical Spastic Paraparesis, among others.

It is another object to provide a pharmaceutical composition having a peptide as an active agent for reducing or inhibiting neuronal cell loss.

These and other objects of the present invention are achieved by a peptciode of the formula

| Leu-Glu-Ser-Tyr-Thr | (SEQ. ID NO: 1) | or

| Ile-Lys-Glu-Tyr-Phe-Thr-Ser | (SEQ. ID: 2) |

A method for treating the symptoms associated with neuronal cell death in a person caused by a neurological degenerative disease comprises administering a therapeutically effective amount of a peptide of the formula

| Leu-Glu-Ser-Tyr-Thr | (SEQ. ID NO: 1) | or

| Ile-Lys-Glu-Tyr-Phe-Thr-Ser | (SEQ. ID NO: 2) |

The invention comprises a peptide of the formula Leu-Glu-Ser-Tyr-Thr (SEQ. ID NO:1) or Ile-Lys-Glu-Tyr-Phe-Thr-Ser (SEQ. ID NO: 2) or a physiologically acceptable salt thereof. A pharmaceutical composition comprising as a active ingredient at least one peptide of the formula Leu-Glu-Ser-Tyr-Thr (SEQ. ID NO: 1) or Ile-Lys-Glu-Tyr-Phe-Thr-Ser (SEQ. ID NO: 2) or a pharmaceutically, acceptable salt thereof, for treating the symptoms caused by neuronal cell loss. The pharmacutical composition can further comprise a pharmaceutically acceptable carrier.

The invention also includes a method for treating the symptoms caused by a loss of neurons comprising administering to a person suffering from a disease causing neuronal cell loss a therapeutically effective amount of a peptide of formula Leu-Glu-SER-Tyr-Thr (SEQ. ID NO: 1) or Ile-Lys-Glu-Tyr-Phe-Thr-Ser (SEQ. ID NO: 2) or pharmaceutically acccptitble salt thereof. The method can comprise either the formula Leu-Glu-Ser-Tyr-Thr (SEQ. ID NO: 1) or Ile-Lys-Glu-Tyr-Phe-Thr-Ser (SEQ. ID. NO: 2). According to the method, the peptide is administered by oral, intranasal, buccal, parenteral, topical or rectal administration.

DETAILED DESCRIPTION OF THE INVENTION

Figure 1:
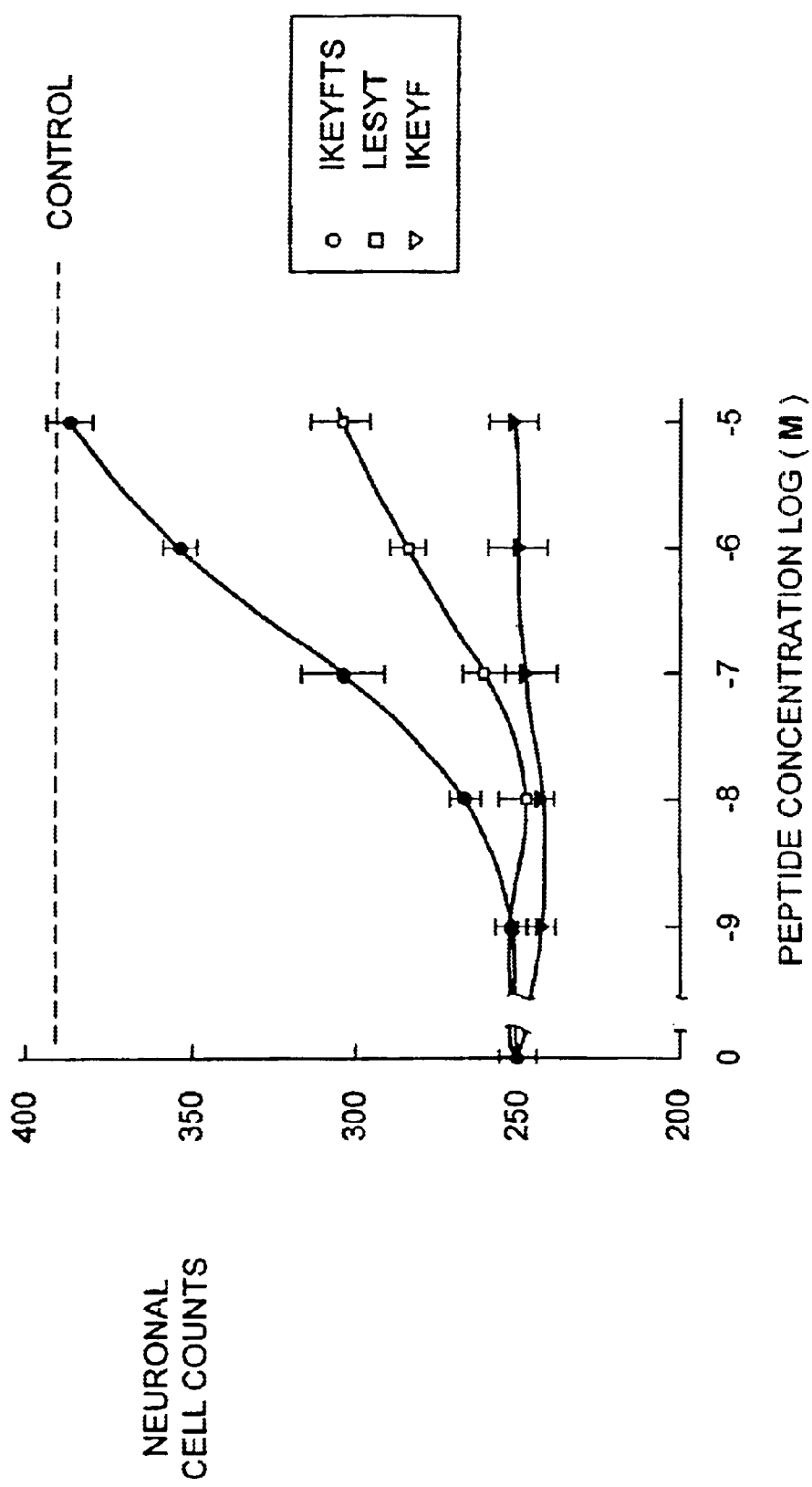
FIG. 1 shows neuronal cell survival with reference to peptide concentration.

Materials: A gp120 isolate RFII was obtained from Dr. P. Nara, NCI, NIH. All of the gp120's are purified, >95% homogeneous and previously tested for neurotoxicity with cultured neurons and were used at 1 pM final concentration in cultures of neurons. Peptides of the formula Ile-Lys-Glu-Tyr-Phe-Thr-Ser (SEQ. ID NO: 2), Ile-Lys-Glu-Tyr-Phe (SEQ. ID NO: 3), and Leu-Glu-Ser-Tyr-Thr (SEQ. ID NO: 1), were obtained from Peninsula Labs, CA. and synthesized by solid-phase Merrified methods and purified to greater than 95% homogeneity by two HPLC methods and structure confirmed by MASS Spectroscopy Analysis.

Neuronal cell culture: Dissociated hippocampal cultures are prepared from neonatal (day 2) rat cortex and hippocampus by known methods. Sterilely dissected brain tissue is minced and treated with 0.125% trypsin for 30 minutes then gently triturated with fire-polished Pasteur pipes and plated in six-well trays (35 mm$^2$) at low density (50,000 cells/35 mm$^2$ dish) upon confluent layers of astrocytes in medium containing D-MEM, penicillin (25 U/ml), streptomycin (25 mg/ml), D-glucose (0.6%), and 10% heat-inactivated fetal calf serum (HyClone Laboratories), supplemented with insulin, transferrin, selenium, corticosterone, and triiodothyronine. Medium is changed after 3 days. At 6 days, half the medium is exchanged for fresh medium. The astrocyte feeder layers were prepared from the cortexes of neonatal rats following dissection and trituration. Plating was 2.5×10$^2$ cells per well. Feeder layers were grown in Eagles's minimal essential medium (Formula No. 82-0234DJ, Gibco) with 10% fetal calf serum until confluent (7–14 days). With this medium the feeder cultures were free of neurons and consisted of flat cells that were stained by antibodies to glial fibrillary acidic protein, a standard immunocytochemical marker for astroglia. When hippocampal or cortical cells were added to the confluent feeder layer, the medium was changed to the following composition: 5% horse serum and MEM supplement with defined medium components. The hippocampal or cortical cultures were treated with 5'-fluoro-2'-deoxyuridine (15 ug/ml plus uridine, 35 ug/ml) to suppress the overgrowth of background cells and allow the establishment of neurons. The neurons in these cultures are post-mitotic. The neuronal cultures were allowed to grow for 1 week prior to the beginning of the experimental period. Before treating the cultures, a complete change of medium was given.

Neuronal survival assay: GP120's, with or without added peptides, were diluted in phosphate buffered saline and added to the cultures, which were treated only once for a four day period. At termination, cultures were fixed with glutaraldehyde as previously described. At the end of the test period, neuronal survival was assessed by immunohistochemical detection of neuron-specific enolase positive cells (neurons). Cultures were counted in a blinded fashion without knowledge of sample treatment in 40 fields at pre-determined coordinate locations. The total area counted is 50 mm$^2$. Each value reported is the mean±the standard error of 3–4 determinations. Control (saline treated) wells from these cultures have 395±20 neurons. Statistical comparisons between experimental and control culture neuronal cell counts are via analysis of variance with the Student-Newman-Kuels multiple comparison of means test.

Results

Effects of Short Chemokine Derived Peptides on GP120-Mediated Neurotoxicity

When the peptides were added to primary cultures of mixed rat neurons glia, together with 1 pM gp120 (RF isolate), which by itself killed about half the neurons in the dish (FIG. 1), neuronal death could be inhibited. In a dose-dependent fashion, significant increases in cell counts were observed from cultures treated with gp120 alone, with IKEYFTS (SEQ. ID NO: 2) and LESYT (SEQ. ID NO: 1) preventing neuronal loss caused by gp120. The peptide IKEYFTS (SEQ. ID NO: 2) had an EC50 of 100 nM and was fully protective at 10 $\mu$M, while LESYT (SEQ. ID NO: 1) was partially protective at 10 $\mu$M. Specificity is shown in that the shorter pentapeptide IKEYF (SEQ. ID NO: 3) was inactive. The dotted line in FIG. 1 represents the mean number of neurons in control cultures.

The peptides also supported the viability of neurons in the absence of added gp120 and thus acted as survival factors. The results thereby identify novel, short chemokine related peptides which have significant neuroprotective activity against gp120 neurotoxicity as well as promote neuronal survival and which therefore may be treatments for AIDS and other neurodegenerative diseases which includes, but is not limited to conditions like Alzheimers, multiple sclerosis, tropical paraparesis, PML and neuropathies of various etiologies including diseases resulting from or relating to HTLV-1 infection, to cite some examples.

The peptides may be administered in suitable carriers by various routes including oral, buccal, iv, rectal, nasal, with effective doses from 0.01 mg to 1000 mgs per day, preferably from 0.2 to 10 mg per day for a 70 kg person.

The active compounds of the invention may exist as physiologically acceptable salts of the peptides.

The compounds of the invention may be beneficially modified by methods known to enhance passage of molecules across the blood-brain barrier. Acetylation has proven to be especially useful for enhancing binding activity of the peptide. The terminal amino and carboxy sites are particularly preferred sites for modification.

The peptides of this invention may also be modified in a constraining conformation to provide improved stability and oral availability.

Unless otherwise indicated the amino acids are, of course, the natural form of L-stereoisomers.

The peptides that are to be administered intranasally in accordance with the invention may be produced by conventional methods of peptide synthesis. Both solid phase and liquid phase methods, as well as other methods e.g., enzymatic methods, may be used. We have found the solid phase method of Merrifield to be particularly convenient. In this process the peptide is synthesized in a stepwise manner while the carboxy end of the chain is covalently attached to an insoluble support. During the intermediate synthetic stages the peptide remains in the solid phase and therefore can conveniently manipulated. The solid support is a chloromethylated styrene-divinylbenzene copolymer.

As an aspect of the invention, therefore, we provide a pharmaceutical compositions comprising a peptide compound of the invention in association with pharmaceutically acceptable carrier or excipient, adapted for use in human or veterinary medicine. Such compositions may be presented for use in a conventional manner in admixture with one or more physiologically acceptable carriers of excipient. The compositions may optionally further contain one or more other therapeutic agents which may, if desired, be a different antiviral agent.

Thus, the peptides according to the invention may be formulated for oral, intranasal, buccal, parenteral, topical or rectal administration.

In particular, the peptides according to the invention may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g., sterile, pyrogen-free water, before use. In a particularly preferred embodiment, the active ingredient may be administered intranasally, preferably in more than one daily application.

The pharmaceutical compositions according to the invention may also contain other active ingredients such as antimicrobial agents, or preservatives.

A further aspect of this invention relates to vaccine preparations containing a peptide according to the invention, to provide protection against viral infection. The vaccine will contain an effective immunogenic amount of peptide, e.g. 1 μg to 20 mg/kg of host, optionally conjugated to a protein such as human serum albumin, in a suitable vehicle, e.g. sterile water, saline or buffered saline. Adjuvants may be employed, such as aluminum hydroxide gel. Administration may be by injection, e.g. intramuscularly, interperitoneally, subcutaneously or intravenously. Administration may take place once or at a plurality of times, e.g. at 1–4 week intervals.

Antigenic sequences from crab as well as proteins from other invertebrates can also be added to the peptides of the invention to promote antigenicity.

What is claimed is:

1. A peptide of the formula Leu-Glu-Ser-Tyr-Thr (SEQ. ID NO: 1) or Ile-Lys-Glu-Tyr-Phe-Thr-Ser (SEQ. ID NO: 2).

2. A pharmaceutical composition comprising as an active ingredient at least one peptide of the formula Leu-Glu-Ser-Tyr-Thr (SEQ. ID NO: 1) or Ile-Lys-Glu-Tyr-Phe-Thr-Ser (SEQ. ID NO: 2) or a pharmaceutically acceptable salt thereof.

3. The pharmaceutical composition of claim 2 further comprising a pharmaceutically acceptable carrier.

4. A method for treating the symptoms caused by GP120 mediated neurotoxicity comprising administering to a person suffering from HIV infection a therapeutically effective amount of a peptide of formula Leu-Glu-Ser-Tyr-Thr (SEQ. ID NO: 1) or Ile-Lys-Glu-Tyr-Phe-Thr-Ser (SEQ. ID NO: 2).

5. The method of claim 4 wherein the formula is Leu-Glu-Ser-Tyr-Thr (SEQ. ID NO: 1).

6. The method of claim 4 wherein the formula is Ile-Lys-Glu-Tyr-Phe-Thr-Ser (SEQ. ID NO: 2).

7. The method of claim 4 wherein the peptide is administered by oral, intranasal, buccal, parenteral, topical, or rectal administration.

8. The method of claim 4 wherein the peptide is administered at from 0.01 mg to 1000 mgs per day.

9. The method of claim 4 wherein the peptide is administered at from 0.2 mg to 10 mg per day.

10. A method for treating the symptoms caused by a loss of neurons resulting from Alzheimer's disease comprising administering a therapeutically effective amount of a peptide of formula Leu-Glu-Ser-Tyr-Thr (SEQ. ID NO: 1) or Ile-Lys-Glu-Tyr-Phe-Thr-Ser (SEQ. ID NO: 2).

* * * * *